United States Patent [19]

Bernardi et al.

[11] 4,166,848

[45] Sep. 4, 1979

[54] ANTHRACYCLINE DERIVATIVES, THEIR PREPARATION AND USE

[75] Inventors: Luigi Bernardi; Paolo Masi; Antonino Suarato, all of Milan; Federico Arcamone, Nerviano, all of Italy

[73] Assignee: Societa Farmaceutici Italia S.p.A., Milan, Italy

[21] Appl. No.: 850,933

[22] Filed: Nov. 14, 1977

[30] Foreign Application Priority Data

Nov. 16, 1976 [GB] United Kingdom ............... 47601/76

[51] Int. Cl.² .................... A61K 31/70; C07G 11/00; C07G 3/00
[52] U.S. Cl. .................................... 424/180; 260/463; 260/590 FB; 536/4; 536/17 A
[58] Field of Search .............. 536/4 A, 17 A; 424/180

[56] References Cited

U.S. PATENT DOCUMENTS

| 4,067,969 | 1/1978 | Penco et al. ......................... 424/180 |
| 4,107,423 | 8/1978 | Arcamone et al. ..................... 536/17 |

OTHER PUBLICATIONS

Arcamone et al., Journ. Med. Chem. vol, 17, No. 3, pp. 335-337 (1974).

Primary Examiner—Ethel G. Love
Attorney, Agent, or Firm—Hubbell, Cohen, Stiefel & Gross

[57] ABSTRACT

Disclosed are antitumor compounds of the formula:

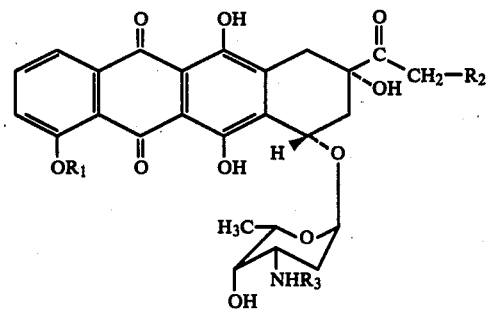

wherein $R_1$ is a $C_2$-$C_4$ alkyl; a $C_3$-$C_6$ cycloalkyl; a $C_3$-$C_6$ cycloalkyl substituted by a halogen, hydroxy, methoxy, amino or dimethylamino group; phenyl or phenyl substituted with nitro, chlorine or methoxy; thiazyl, pyridyl, pyrazyl; or a phenyl-alkyl group of the formula X—Phe—$(CH_2)_n$—, in which X is hydrogen, halogen, hydroxyl, amino, or nitro and n is an integer from 1 to 2; $R_2$ is hydrogen, hydroxyl or acyloxy (R—COO—), where R is an alkyl having from 1 to 11 carbon atoms; and $R_3$ is hydrogen or trifluoroacetyl and salts thereof with pharmaceutically acceptable acids. Compounds I are prepared by condensing the aglycones thereof with 2,3,6-trideoxy-3-trifluoroacetamido-4-O-trifluoro-acetyl-α-L-lyxopyranosyl chloride according to a conventional technique.

8 Claims, No Drawings

ANTHRACYCLINE DERIVATIVES, THEIR PREPARATION AND USE

The invention described herein was made in the course of work under a grant from the United States Department of Health, Education and Welfare.

CROSS-REFERENCE TO RELATED APPLICATIONS

This application is related to and incorporates by reference the contents of co-pending application, Ser. No. 579,901, filed May 22, 1975, now U.S. Pat. No. 4,046,878, and owned by the unrecorded assignee hereof.

BACKGROUND OF THE INVENTION

1. Field of the Invention

The present invention relates to new antitumor agents, novel intermediates used to make the new agents, a process for the preparation of said intermediates and the use of the new antitumor agents in treating tumor diseases.

2. The Prior Art

The antitumor antibiotic daunomycin, as well as its aglycone (daunomycinone formula IV, below) are known compounds. Moreover, U.S. Pat. No. 3,803,124, owned by the unrecorded assignee hereof, describes a process for making daunomycin from daunomycinone.

SUMMARY OF THE INVENTION

The invention provides, in one aspect thereof, a new class of antitumor antibiotics of the formula I:

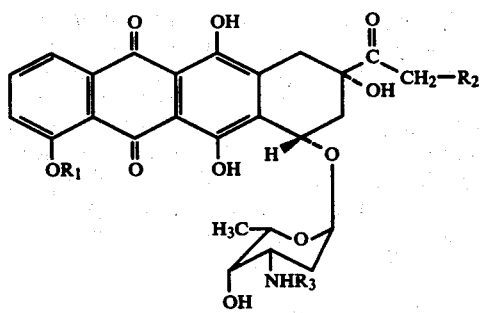

wherein $R_1$ is a $C_2$-$C_4$ alkyl; a $C_3$-$C_6$ cycloalkyl; a $C_3$-$C_6$ cycloalkyl substituted by a halogen, hydroxy, methoxy, amino or dimethylamino group; phenyl or phenyl substituted with nitro, chlorine or methoxy; thiazyl, pyridyl, pyrazyl; or phenyl-alkyl group of the formula X—Phe—$(CH_2)_n$—, in which X is hydrogen, halogen, hydroxyl, amino or nitro, and n is an integer from 1 to 2; $R_2$ is hydrogen, hydroxyl or acyloxy (R—COO—), where R is an alkyl having from 1 to 11 carbon atoms; and $R_3$ is hydrogen or trifluoroacetyl and salts thereof with pharmaceutically acceptable acids.

The synthesis of the compounds of formula I is effected by a conventional procedure starting from the aglycones III (which are novel analogues of the known compound daunomycinone),

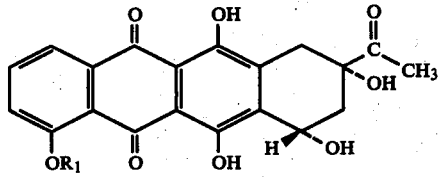

wherein $R_1$ is as defined above. Thus, in another aspect, the invention provides these novel aglycones III. The compounds of the formula I wherein $R_2$ is H are obtained by condensing an aglycone of the formula III with the appropriate sugar moiety. The compounds of formula I ($R_2$=H) are then transformed into compounds of formula I wherein $R_2$ is hydroxyl or acyloxy according to a procedure heretofore applied to the daunomycin molecule itself, and which is described in U.S. Pat. No. 3,803,124.

While the process for making compounds I from the aglycones III is not new, the process by which said aglycones III themselves are made is novel and is part of this invention. Thus, the invention provides, in yet another aspect thereof, a new process for preparing the aglycones III. This process is outlined in the following reaction scheme:

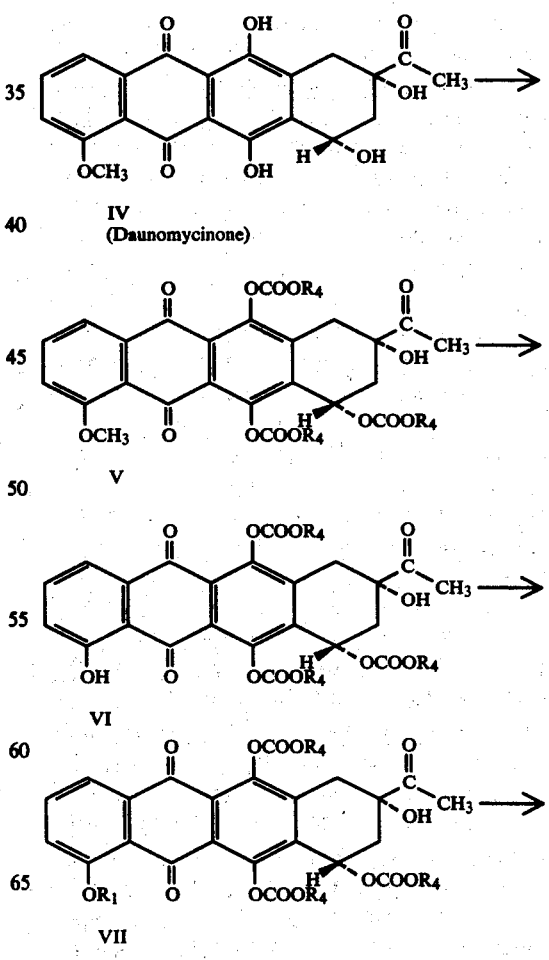

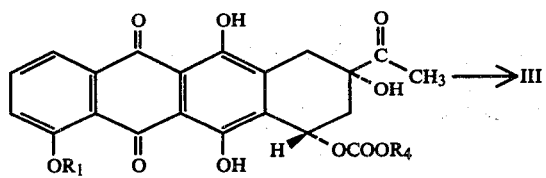

VIII

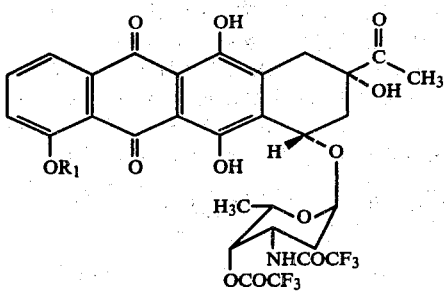

IX

In formulae IV, V, VI, VII and VIII, $R_1$ is as defined above and $R_4$ is an alkyl group, the exact nature of which is not critical because, as will be shown below, it is merely a "protecting" group which is eventually removed. In practice, however, $R_4$ will usually be ethyl because compound IV (daunomycinone) is preferably reacted with ethylorthoformate in order to protect the 6, 7 and 11 positions.

According to the process for preparing aglycones III, daunomycinone IV is readily transformed into the 6,7,11-trialkoxycarbonyl derivative V (itself a novel intermediate forming part of the invention) by a reaction carried out at room temperature with an alkylchloroformate, preferably, ethylorthoformate, in the presence of a base such as pyridine. Treatment of V with aluminum tribromide in a suitable organic solvent, such as dichloromethane, chloroform, benzene and the like, affords the demethyl analogues VI, which is a key intermediate in the synthesis of III. Analogues VI, therefore also form part of the invention. The reaction of VI with a halide of the formula $R_1$—Y, wherein $R_1$ is as defined above and Y is Cl, Br or I, in the presence of a base such as silver oxide, potassium carbonate and the like, in an organic solvent and at a temperature in the range of 10° to 100° C., yields the new intermediate compounds VIII (also forming part of the invention).

The latter, i.e., compounds VII, on treatment with a weak organic base, preferably a secondary amine such as morpholine, methylpiperazine and the like, affords the further novel derivatives VIII (also forming part of the invention), in which only the phenolic protecting groups at positions 6 and 11 have been removed. The final step involves a mild hydrolysis of VIII with a dilute inorganic base to remove the protecting group at the 7-position and thereby yield the new aglycones of formula III.

The biologically active glycosides of formula I wherein $R_2$ is H are prepared from the aglycones III according to the procedure described in co-pending application, Ser. No. 579,901, filed May 22, 1975, now U.S. Pat. No. 4,046,878, and owned by the unrecorded assignee hereof. Thus, according to that procedure, the aglycones of the formula III are condensed with 2,3,6-trideoxy-3-trifluoroacetamido-4-O-trifluoroacetyl-α-L-lyxopyranosyl chloride in the presence of a silver salt or silver oxide to form the intermediates IX, which, upon being treated with methanol, are converted into the compounds of formula I, wherein $R_2$ is H and $R_3$ is $CF_3CO$.

Subsequent mild hydrolysis of compounds I ($R_2$=H, $R_3$=$CF_3CO$) with dilute alkaline bases yields the corresponding glycosides I ($R_2$=H, $R_3$=H).

The latter products are converted into I ($R_2$=hydroxy or or acyloxy group, $R_3$=H) following the procedure used for the functionalization of the 14-position of duanomycin which is described in U.S. Pat. No. 3,803,124, owned by the unrecorded assignee hereof.

The new compounds of the formula I, wherein $R_1$, $R_2$ and $R_3$ are as defined above have antimitotic activity which makes them useful therapeutic agents for the treatment of tumor diseases. Accordingly, in another aspect, the invention provides methods for treating such diseases using the novel compounds of formula I.

DESCRIPTION OF THE PREFERRED EMBODIMENTS

The following examples are given to illustrate the preparation of the compounds according to the invention without, however, limiting the invention. All parts given are by weight, unless otherwise indicated.

EXAMPLE 1

$O^6, O^7, O^{11}$-Triethoxycarbonyldaunomycinone 20 ml. of ethylchlorocarbonate were added dropwise over 30 minutes to a stirred solution of 10 g. of daunomycinone in 50 ml. of pyridine. After 1 hour the reaction mixture was poured into ice water and neutralized with 1 N hydrochloric acid. The resulting precipitate was collected by filtration, dissolved in chloroform and dried over anhydrous $Na_2SO_4$. The solvent was distilled off in vacuo and the residue was crystallized from benzene to yield 13 g. of $O^6, O^7, O^{11}$-triethoxycarbonyldaunomycinone.

PMR (CDCl$_3$):
1.45δ (t, 3 CH$_3$—C(H$_2$))
2.33δ (s, CH$_3$—CO)
3.90δ (s, CH$_3$O)
4.40δ (q, 3 CH$_2$—C(H$_3$))
6.15δ (m, C—7—H)
7.03-7.76δ (m, aromatic protons)

EXAMPLE 2

4-Demethoxy-4-hydroxy-$O^6, O^7, O^{11}$-triethoxycarbonyldaunomycinone

A solution of 10 g. of $O^6, O^7, O^{11}$-triethoxycarbonyldaunomycinone in 500 ml. of anhydrous dichloromethane was vigorously flushed with nitrogen while 20 g. of aluminum tribromide were added over 2 hours. After an additional hour, the reaction mixture was poured into a solution of 80 g. of oxalic acid in 1 liter of water. The organic layer was separated, washed with water, dried over anhydrous $Na_2SO_4$ and evaporated to dryness.

The residue was chromatographed on silica gel using chloroform as the solvent to give 6 g. of 4-demethoxy-4-hydroxy-$O^6,O^7,O^{11}$-triethoxycarbonyldaunomycinone.

PMR (CDCl$_3$):
- 1.16–1.76δ (m, 3 CH$_3$—C(H$_2$))
- 2.40δ (s, CH$_3$—CO)
- 3.86–4.66δ (m, 3—O—CH$_2$—C(H$_3$))
- 6.16δ (m, C—7—H)
- 7.0–7.8δ (m, aromatic protons)
- 12.20δ (s, phenolic OH)

EXAMPLE 3

4-Demethoxy-4-ethoxy-$O^6,O^7,O^{11}$-triethoxycarbonyldaunomycinone

A solution of 5 g. of 4-demethoxy-4-hydroxy-$O^6,O^7,O^{11}$-triethoxycarbonyldaunomycinone in 200 ml. of dichloromethane was treated with 8 ml. of ethyl iodide and 4 g. of silver oxide and refluxed for 3 hours. After filtration, the solvent was removed in vacuo and the residue crystallized from benzene to yield 4.5 g. of 4-demethoxy-4-ethoxy-$O^6,O^7,O^{11}$-triethoxycarbonyldaunomycinone. PMR (CDCl$_3$);
- 1.20–1.80δ (m, 4 CH$_3$—C(H$_2$))
- 2.38δ (s, CH$_3$—CO)
- 3.86–4.66δ (m, 4-CH$_2$—C(H$_3$))
- 6.20δ (m, C—7—H)
- 7.0–7.8δ (m, aromatic protons)

EXAMPLE 4

4-Demethoxy-4-ethoxy-7-O-ethoxycarbonyldaunomycinone

A solution of 5 g. of 4-demethoxy-4-ethoxy-$O^6,O^7,O^{11}$-triethoxycarbonyldaunomycinone was treated with 30 ml. of methanolic 0.5 M morpholine at room temperature for 3 hours. The solvent was then removed in vacuo and the residue taken up in chloroform, washed with a solution of oxalic acid in water and then with distilled water. The chloroform was distilled off and the crystalline residue was taken up with diethyl ether and collected by filtration to give 3 g. of 4-demethoxy-4-ethoxy-7-O-ethoxycarbonyldaunomycinone.

PMR (CDCl$_3$):
- 1.36 and 1.60δ (two t, 2 CH$_3$—C(H$_2$)—)
- 2.43δ (s, CH$_3$—CO)
- 4.26δ (q, 2 CH$_2$—C(H$_3$))
- 6.30δ (m, C—7—H)
- 7.13–8.03δ (m, aromatic protons)
- 13.10 and 13.75δ (two s, 2 phenolic OH)

EXAMPLE 5

4-Demethoxy-4-ethoxydaunomycinone

To a solution of 1 g. of 4-demethoxy-4-ethoxy-7-O-ethoxycarbonyldaunomycinone in 20 ml. of dimethylformamide, 100 ml. of aqueous 0.05 N NaOH were added dropwise with stirring at room temperature. After acidification with aqueous oxalic acid and extraction with chloroform, the organic layer was washed with water and evaporated to dryness. The residue was purified by column chromatography (silica gel chloroform/acetone 95/5, v/v) to yield 0.6 g. of 4-demethoxy-4-ethoxydaunomycinone.

PMR (CDCl$_3$):
- 1.53δ (t, CH$_3$—C(H$_2$))
- 2.43δ (s, CH$_3$—CO)
- 4.20δ (q, CH$_2$—C(H$_3$))
- 5.08δ (broad s, C—7—H)
- 7.03–7.93δ (m, aromatic protons)
- 12.86 and 13.56δ (two s, 2 phenolic OH).

EXAMPLE 6

4-Demethoxy-4-ethoxy-N-trifluoroacetyldaunomycin

To a solution of 1.5 g. of 4-demethoxy-4-ethoxydaunomycinone and 1.25 g. of 2,3,6-trideoxy-3-trifluoroacetamido-4-O-trifluoroacetyl-α-L-lyxopyranosyl chloride in 100 ml. of anhydrous dichloromethane a solution of 0.95 g. of silver trifluoromethansulphonate in anhydrous diethyl ether was added dropwise at room temperature under stirring. After 1 hour, the reaction mixture was washed with aqueous NaHCO$_3$ and evaporated to dryness. The residue was dissolved in methanol containing 1 drop of triethylamine and left standing at room temperature for 2 hours. The solvent was removed in vacuo and the residue chromatographed (silica gel; chloroform - acetone 95/5, v/v) to give 0.9 g. of 4-demethoxy-4-ethoxy-N-trifluoroacetyldaunomycin.

PRM (CDCl$_3$):
- 1.59δ (t, CH$_3$—C(H$_2$))
- 2.43δ (s, CH$_3$O)
- 5.18δ (m, C—7—H)
- 5.50δ (m, C—1'—H)
- 7.1–8.05δ (m, aromatic protons)
- 13.23 and 14.06δ (two s, 2 phenolic OH)

EXAMPLE 7

4-Demethoxy-4-ethoxydaunomycin hydrochloride

Five hundred milligrams of 4-demethoxy-4-ethoxy-4-trifluoroacetyldaunomycin were dissolved in 30 ml. of aqueous 0.15 N NaOH and left standing for 1 hour at room temperature. After acidification with oxalic acid and rapid neutralization with aqueous NaHCO$_3$, the product was extracted with water and evaporated to dryness. The residue was dissolved in methylene chloride and treated with 1 equivalent of HCl in methanol. Upon adding diethyl ether, 350 mg. of 4-demethoxy-4-ethoxy-daunomycin hydrochloride precipitated and were collected by filtration.

EXAMPLE 8

4-Demethoxy-4-isopropyloxy-$O^6,O^7,O^{11}$-triethoxycarbonyldaunomycinone

A solution of 7 g. of 4-demethoxy-4-hydroxy-$O^6,O^7,O^{11}$-triethoxycarbonyldaunomycinone in 200 ml. of chloroform was treated with 10 ml. if isopropyliodide and 6 g. of silver oxide and refluxed for 4 hours. After filtration, the solvent was removed in vacuo and the residue crystallized from benzene to yield 5 g. of 4-demethoxy-4-isopropyloxy-$O^6$, $O^7$, $O^{11}$-triethoxycarbonyldaunomycinone.

PMR (CDCl$_3$):
- 1.1–1.7 δ

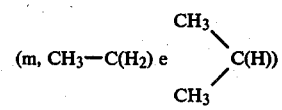

- 2.32δ (s, CH$_3$CO)
- 4.1–4.6δ (m, CH$_2$—C(H$_3$))
- 6.25δ (broad s, C—7—H)
- 7.15–7.9δ (m, 3 aromatic protons)

EXAMPLE 9

4-Demethoxy-4-isopropyloxy-7-O-ethoxycarbonyl-daunomycinone

A solution of 5 g. of 4-demethoxy-4-isopropyloxy-$O^6,O^7O^{11}$-triethoxycarbonyldaunomycinone ,$O^{in}$ 200 ml. of dichloromethane was treated with 30 ml. of an 0.5 M morpholine solution in dichloromethane with stirring at room temperature for 3 hours.

After acidification with aqueous oxalic acid and extraction with dichloromethane, the organic layer was washed with water and evaporated to dryness. The residue was crystallized from diethyl ether, to yield 2.8 g. of 4-demethoxy-4-isopropyloxy-7-O-ethoxycarbonyl-daunomycinone.

EXAMPLE 10

4-Demethoxy-4-isopropyloxydaunomycinone

To a solution of 1 g. of 4-demethoxy-4-isopropyloxydaunomycinone in 20 ml. of acetone, 100 ml. of aqueous 0.05 M NaOH were added dropwise under stirring at room temperature.

After acidification with aqueous oxalic acid and extraction with chloroform, the organic layer was washed with water and evaporated to dryness. The residue was purified by column chromatography (silica gel - chloroform/acetone 95/5) to yield 0.5 g. of 4-demethoxy-4-isopropyloxydaunomycinone.

PMR (CDCl$_3$):
1.37$\delta$

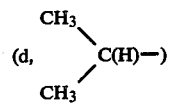

2.25$\delta$ (s, CH$_3$CO)
4.67$\delta$ (m, —O—CH—(CH$_3$)$_2$)
5.20$\delta$ (broad s, C—7—H)
7.1–8.0$\delta$ (m, 3 aromatic protons)
12.95 and 13.85$\delta$ (two s, phenolic hydroxyls)

EXAMPLE 11

4-Demethoxy-4-isopropyloxy-N-trifluoroacetyldaunomycin

To a solution of 1 g. of 4-demethoxy-4-isopropyloxydaunomycinone and 0.95 g. of 2,3,6-trideoxy-3-trifluoroacetamido-4-O-trifluoroacetyl-α-L-hyxopyranosyl chloride in 100 ml. of anhydrous dichloromethane, a solution of 0.80 g. of silver trifluoromethansulfonate in anhydrous diethyl ether was added dropwise at room temperature under stirring. After 1 hour, the reaction mixture was washed with aqueous NaHCO$_3$ and evaporated to dryness. The residue was dissolved in methanol containing 1 drop of triethylamine and left standing at room temperature for 2 hours. The solvent was removed in vacuo and the residue chromatographed (silica gel, chloroform-acetone 95/5, v/v) to give 0.6 g. of 4-demethoxy-4-isopropyloxy-N-trifluoroacetyldaunomycin.

PMR (CDCl$_3$):
1.33$\delta$ (d, CH$_3$—C—5')
1.53$\delta$

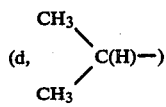

2.43$\delta$ (s, CH$_3$CO)
4.74$\delta$ (m, —O—CH(CH$_3$)$_2$)
5.20$\delta$ (broad s, C—7—H)
5.49$\delta$ (broad s, C—1'—H)
7.1–8.1$\delta$ (m, 3 aromatic protons)
13.15 and 14.05$\delta$ (two s, phenolic hydroxyls)

EXAMPLE 12

4-Demethoxy-4-isopropyloxydaunomycin hydrochloride 0.500 g. of 4-demethoxy-4-isopropyloxy-N-trifluoroacetyldaunomycin was dissolved in 10 ml. of acetone and 30 ml. of aqueous 0.15 M NaOH and left standing for 1 hour at room temperature. After acidification with oxalic acid and rapid neutralization with aqueous NaHCO$_3$, the product was extracted with water and evaported to dryness. The residue was dissolved in methylene chloride and treated with 1 equivalent of HCl in methanol. Upon adding diethyl ether, 0.200 g. of 4-demethoxy-4-isopropyloxydaunomycin hydrochloride precipitated and was collected by filtration.

EXAMPLE 13

4-Demethoxy-4-benzyloxy-$O^6,O^7,O^{11}$-triethoxycarbonyldaunomycinone

A mixture of 8 g. of 4-demethoxy-4-hydroxy-$O^6,O^7$,$O^{11}$-triethylcarbonyldaunomycinone, 8 g. of silver oxide and 8 ml. of benzyl-bromide in 200 ml. of dichloromethane was refluxed for 4 hours. After filtration, the solvent was removed in vacuo and the residue chromatographed (silica gel, dichloromethane) to give, after crystallization from benzene, 7 g. of 4-demethoxy-4-benzyloxy-$O^6,O^7,O^{11}$-triethoxydarbonyldaunomycinone.

PMR (CDCl$_3$):
1.1–1.8$\delta$ (m, 3CH$_3$—C(H$_2$))
2.36$\delta$ (s, CH$_3$CO)
4.0–4.65$\delta$ (m, 3CH$_2$—C(H$_3$))
5.20$\delta$ (s, CH$_2$O)
6.25$\delta$ (broad s, C—7—H)
7.0–7.9$\delta$ (m, 8 aromatic protons)

EXAMPLE 14

4-Demethoxy-4-benzyloxy-7-O-ethoxycarbonyl-daunomycinone

To a solution of 6 g. of 4-demethoxy-4-benzyloxy-$O^6,O^7,O^{11}$-triethoxycarbonyldaunomycinone in 20 ml. of chloroform and 80 ml. of benzene, there were added dropwise under stirring at room temperature, 50 ml. of an 0.5 M benzene solution of morpholine. The mixture was taken up in benzene and washed with aqueous oxalic acid. The organic layer was washed with water and evaporated to dryness. The residue was crystallized from diethyl ether to yield 3 g. of 4-demethoxy-4-benzyloxy-7-O-ethoxycarbonyldaunomycinone.

PMR (CDCl$_3$):
1.36$\delta$ (t, CH$_3$—C(H$_2$))
2.40$\delta$ (s, CH$_3$CO)
4.27$\delta$ (q, CH$_2$—C(H$_3$))

5.10δ (s, CH₂—O)
6.15δ (broad s, C—7—H)
7.0–7.9δ (m, 8 aromatic protons)
13.00 and 13.75δ (two s, phenolic hydroxyls)

EXAMPLE 15

4-Demethoxy-4-benzyloxydaunomycinone

Operating as in Example 5, and starting from 3 g. of 4-demethoxy-7-benzyloxy-7-O-ethoxycarbonyldaunomycinone, there were obtained 2.1 g. of 4-demethoxy-4-benzyloxydaunomycinone.
PMR (CDCl₃):
2.33δ (s, CH₃CO)
5.10δ (s, CH₂—O)
6.9–7.8δ (m, 8 aromatic protons)
12.85 and 13.70δ (two s, phenolic hydroxyls)

EXAMPLE 16

4-Demethoxy-4-benzyloxy-N-trifluoroacetyldaunomycin

Operating as in Example 6, and starting from 1 g. of 4-demethoxy-4-benzyloxydaunomycinone, there was obtained 0.35 g. of 4-demethoxy-4-benzyloxy-N-trifluoroacetyldaunomycin.
PMR (CDCl₃):
1.31δ (d, CH₃—C(H))
2.38δ (s, CH₃—CO)
4.95δ (s, CH₂—O)
5.20δ (broad s, C—7—H)
5.45δ (broad s, C—1'—H)
6.7–8.0δ (m, 8 aromatic protons)
12.95 and 13.90δ (two s, phenolic hydroxyls)

EXAMPLE 17

4-Demethoxy-4-benzyloxydaunomycin hydrochloride 0.5 g. of 4-demethoxy-4-benzyloxy-N-trifluoroacetyldaunomycin was treated with dilute NaOH according to the procedure described in Example 7 to give 0.2 g. of 4-demethoxy-4-benzyloxydaunomycin hydrochloride.

EXAMPLE 18

4-Demethoxy-4-cyclohexyloxy-O⁶,O⁷,O¹¹-triethoxycarbonyldaunomycinone

A mixture of 9 g. of 4-demethoxy-4-hydroxy-O⁶,O⁷,O¹¹-triethoxycarbonyldaunomycinone, 10 g. of silver oxide and 10 ml. of cyclohexyliodide in 200 ml. of chloroform, was refluxed for 4 hours. After filtration, the solvent was removed in vacuo and the residue chromatographed (silica gel, dichloromethane) to give 6 g. of 4-demethoxy-4-cyclohexyloxy-O⁶,O⁷,O¹¹-triethoxycarbonyldaunomycinone.
PMR (CCl₄):
1.0–2.3δ (m, CH₃—C(H₂) and cyclohexane CH₂)
3.8–4.7δ (m, CH₂—C(H₃))
6.0δ (broad s, C—7—H)
6.8–7.7δ (m, 3 aromatic protons)

EXAMPLE 19

4-Demethoxy-4-cyclohexyloxy-7-O-ethoxycarbonyldaunomycinone 6 g. of 4-demethoxy-4-cyclohexyloxy-O⁶,O⁷,O¹¹-triethoxycarbonyldaunomycinone were treated with morpholine according to the procedure described in Example 4 to give 3.1 g. of 4-demethoxy-4-cyclohexyloxy-7-O-ethoxycarbonyldaunomycinone.
PMR (CDCl₃):
1.0–2.3δ (m, cyclohexane CH₂ and CH₃—C(H₂))
2.44δ (s, CH₃CO)
4.25δ (q, CH₂—C(H₃))
6.25δ (broad s, C—7—H)
7.15–8.05δ (m, 3 aromatic protons)
13.0–14.0δ (two s, phenolic hydroxyls)

EXAMPLE 20

4-Demethoxy-4-cyclohexyloxydaunomycinone 3.1 g. of 4-demethoxy-4-cyclohexyloxy-7-O-ethoxycarbonyldaunomycinone were hydrolyzed with dilute NaOH according to the procedure described in Example 5 to give 1.7 g. of 4-demethoxy-4-cyclohexyloxydaunomycinone.
PMR (CDCl₃):
1.0–2.5δ (m, cyclohexane CH₂)
2.42δ (s, CH₃CO)
3.82δ (broad s, cyclohexane CH)
5.33δ (broad s, C—7—H)
7.25–8.16δ (m, 3 aromatic protons)
13.20 and 14.15δ (two s, phenolic hydroxyls)

EXAMPLE 21

4-Demethoxy-4-cyclohexyloxy-N-trifluoroacetyldaunomycin 1.2 g. of 4-demethoxy-4-cyclohexyloxydaunomycinone were condensed with 2,3,6-trideoxy-3-trifluoroacetamido-4-O-trifluoroacetyl-α-L-lyxopyranosyl chloride according to the procedure described in Example 6 to give 0.5 g. of 4-demethoxy-4-cyclohexyloxy-N-trifluoroacetyldaunomycin.
PMR (CDCl₃):
1.0–2.6δ (m, cyclohexane CH₂)
2.44δ (s, CH₃CO)
5.10δ (broad s, C—7—H)
5.46δ (broad s, C—1'—H)
6.85–8.00δ (m, 3 aromatic protons)
13.10 and 14.20δ (two s, phenolic hydroxyls)

EXAMPLE 22

4-Demethoxy-4-cyclohexyloxydaunomycin hydrochloride

Operating as in Example 7, and starting from 0.5 g. of 4-demethoxy-4-cyclohexyloxy-N-trifluoroacetyldaunomycin, there was obtained 0.18 g. of 4-demethoxy-4-cyclohexyloxydaunomycin hydrochloride.

EXAMPLE 23

4-Demethoxy-4-n-propyloxy-O⁶,O⁷,O¹¹-triethoxycarbonyldaunomycinone

A solution of 7 g. of 4-demethoxy-4-hydroxy-O⁶,O⁷,O¹¹-triethoxycarbonyldaunomycinone in 200 ml. of chloroform was treated with 10 ml. of n-propyl iodide and 6 g. of silver oxide and refluxed for 4 hours. After filtration, the solvent was removed in vacuo and the residue crystallized from benzene to yield 4.8 g. of 4-demethoxy-4-n-propyloxy-O⁶,O⁷,O¹¹-triethoxycarbonyldaunomycinone.

EXAMPLE 24

4-Demethoxy-4-n-propyloxy-7-O-ethoxycarbonyldaunomycinone

A solution of 4.5 g. of 4-demethoxy-4-n-propyloxy-O⁶,O⁷,O¹¹-triethoxycarbonyldaunomycinone in 200 ml. of dichloromethane was treated with 30 ml. of an 0.5 M morpholine solution in dichloromethane at room temperature for 3 hours under stirring. After acidification with aqueous oxalic acid and extraction with dichloromethane, the organic layer was washed with water and evaporated to dryness. The residue was crystallized from diethyl ether to yield 2.7 g. of 4-demethoxy-4-n-isopropyloxy-7-O-ethoxycarbonyldaunomycinone.

EXAMPLE 25

4-Demethoxy-4-n-propyloxydaunomycinone

To a solution of 2 g. of 4-demethoxy-4-n-propyloxydaunomycinone in 40 ml. of acetone, 200 ml. of aqueous 0.05 M NaOH were added dropwise under stirring at room temperature. After acidification with aqueous oxalic acid and extraction with chloroform, the organic layer was washed with water and evaporated to dryness. The residue was purified by column chromatography (silica gel-chloroform-acetone 95/5, v/v) to yield 1 g. of 4-demethoxy-4-n-propyloxydaunomycinone.

EXAMPLE 26

4-Demethoxy-4-n-propyloxy-N-trifluoroacetyldaunomycin

To a solution of 1 g. of 4-demethoxy-4-n-propyloxydaunomycinone and 0.95 g. of 2,3,6-trideoxy-3-trifluoroacetamido-4-O-trifluoroacetyl-α-L-lyxopyranosyl chloride in 100 ml. of anhydrous dichloromethane, a solution of 0.8 g. of silver trifluoromethanesulfonate in anhydrous diethyl ether was added dropwise, under stirring, at room temperature. After 1 hour, the reaction mixture was washed with aqueous NaHCO$_3$ and evaporated to dryness. The residue was dissolved in methanol containing 1 drop of triethylamine and left standing at room temperature for 2 hours. The solvent was removed in vacuo and the residue chromatographed (silica gel-chloroform/acetone 95/5, v/v) to give 0.5 g. of 4-demethoxy-4-n-propyloxy-N-trifluoroacetyldaunomycin.

EXAMPLE 27

4-Demethoxy-4-n-propyloxydaunomycin hydrochloride 0.500 g. of 4-demethoxy-4-n-propyloxy-N-trifluoroacetyldaunomycin was dissolved in 10 ml. of acetone and 30 ml. of aqueous 0.15 M NaOH and left standing for 1 hour at room temperature. After acidification with oxalic acid and neutralization with aqueous NaHCO$_3$, the product was extracted with water and the aqueous solution evaporated to dryness in vacuo. The residue was dissolved in methylene chloride and treated with 1 equivalent of HCl in methanol. By adding diethyl ether, 0.180 g. of 4-demethoxy-4-n-propyloxydaunomycin hydrochloride precipitated and was collected by filtration.

EXAMPLE 28

4-Demethoxy-4-n-butyloxy-O$^6$,O$^7$,O$^{11}$-triethoxycarbonyldaunomycinone 5 g. of 4-demethoxy-4-hydroxy-O$^6$,O$^7$,O$^{11}$-triethoxycarbonyldaunomycinone were treated with n-butyl iodide and silver oxide, as described in Example 3 to give 3.4 g. of 4-demethoxy-4-n-butyloxy-O$^6$,O$^7$,O$^{11}$-triethoxycarbonyldaunomycinone.

EXAMPLE 29

4-Demethoxy-4-n-butyloxy-7-O-ethoxycarbonyldaunomycinone 3 g. of 4-demethoxy-4-n-butyloxy-O$^6$,O$^7$,O$^{11}$-triethoxycarbonyldaunomycinone were treated with an 0.5 M methanolic morpholine solution according to the procedure described in Example 4. Thereby, 1.7 g. of 4-demethoxy-4-n-butyloxy-7-O-ethoxycarbonyldaunomycinone were obtained.

EXAMPLE 30

4-Demethoxy-4-n-butyloxydaunomycinone 1.7 g. of 4-demethoxy-4-n-butyloxy-7-O-ethoxycarbonyldaunomycinone were treated with dilute NaOH as described in Example 5 to give 0.8 g. of 4-demethoxy-4-n-butyloxydaunomycinone.

EXAMPLE 31

4-Demethoxy-4-n-butyloxy-N-trifluoroacetyldaunomycin 1.5 g. of 4-demethoxy-4-n-butyloxydaunomycinone were reacted with 1.45 g. of 2,3,6-trideoxy-3-trifluoroacetamido-4-O-trifluoroacetyl-α-L-lyxopyranosyl chloride in anhydrous dichloromethane and in the presence of 1.2 g. of silver trifluoromethansulfonate, according to the procedure described in Example 6. 0.90 g. of 4-demethoxy-4-n-butyloxy-N-trifluoroacetyldaunomycin was obtained.

EXAMPLE 32

4-Demethoxy-4-n-butyloxydaunomycin hydrochloride 0.8 g. of 4-demethoxy-4-n-butyloxy-N-trifluoroacetyldaunomycin was hydrolyzed with an aqueous 0.15 M NaOH solution as described in Example 7 to give 0.3 g. of 4-demethoxy-4-n-butyloxydaunomycin hydrochloride.

EXAMPLE 33

4-Demethoxy-4-sec.butyloxy-O$^6$,O$^7$,O$^{11}$-triethoxycarbonyldaunomycinone 4 g. of 4-demethoxy-4-hydroxy-O$^6$,O$^7$,O$^{11}$-triethoxycarbonyldaunomycinone were treated with sec. butyl iodide and silver oxide as described in Example 3 to give 2.5 g. of 4-demethoxy-4-sec.butyloxy-O$^6$,O$^7$,O$^{11}$-triethoxycarbonyldaunomycinone.

EXAMPLE 34

4-Demethoxy-4-sec.butyloxy-7-O-ethoxycarbonyldaunomycinone 2.4 g. of 4-demethoxy-4-sec.butyloxy-O$^6$,O$^7$,O$^{11}$-triethoxycarbonyldaunomycinone were treated with an 0.5 M methanolic morpholine solution as described in Example 4. 1.3 g. of 4-demethoxy-4-sec.butyloxy-7-O-ethoxycarbonyldaunomycinone were isolated.

EXAMPLE 35

4-Demethoxy-4-sec.butyloxydaunomycinone 1.2 g. of 4-demethoxy-4-sec.butyloxy-7-O-triethoxycarbonyldaunomycinone were treated with dilute NaOH as described in Example 5 to give 0.5 g. of 4-demethoxy-4-sec.butyloxydaunomycinone.

EXAMPLE 36

4-Demethoxy-4-sec.butyloxy-N-trifluoroacetyldaunomycin 0.4 g. of 4-demethoxy-4-sec.butyloxydaunomycinone was reacted with 0.39 g. of 2.3.6-trideoxy-3-trifluoroacetamido-4-O-trifluoroacetyl-α-L-lyxopyranosyl chloride in the presence of 0.3 g. of silver trifluoromethansulfonate, as described in Example 6, to give 0.2 g. of 4-demethoxy-4-sec.butyloxy-N-trifluoroacetyldaunomycin.

EXAMPLE 37

4-Demethoxy-4-sec.butyloxydaunomycin hydrochloride 0.15 g. of 4-demethoxy-4-sec.butyloxy-N-trifluoroacetyldaunomycin was treated with an aqueous 0.15 M NaOH solution as described in Example 7 to give 0.05 g. of 4-demethoxy-4-sec.butyloxydaunomycin hydrochloride.

EXAMPLE 38

4-Demethoxy-4-isobutyloxy-$O^6,O^7,O^{11}$-triethoxycarbonyldaunomycinone 8 g. of 4-demethoxy-4-hydroxy-$O^6,O^7,O^{11}$-triethoxycarbonyldaunomycinone were treated with isobutyl iodide and silver oxide as described in Example 3, to give 5 g. of 4-demethoxy-4-isobutyloxy-$O^6,O^7,O^{11}$-triethoxycarbonyldaunomycinone.

EXAMPLE 39

4-Demethoxy-4-isobutyloxy-7-O-ethoxycarbonyldaunomycinone 4 g. of 4-demethoxy-4-isobutyloxy-$O^6,O^7,O^{11}$-triethoxycarbonyldaunomycinone were treated with an 0.5 M methanolic morpholine solution as described in Example 4. 2.0 g. of 4-demethoxy-4-isobutyloxy-7-O-ethoxycarbonyldaunomycinone were obtained.

EXAMPLE 40

4-Demethoxy-4-isobutyloxydaunomycinone 1.9 g. of 4-demethoxy-4-isobutyloxy-7-O-ethoxycarbonyldaunomycinone were treated with dilute NaOH as described in Example 5 to give 0.8 g. of 4-demethoxy-4-isobutyloxydaunomycinone.

EXAMPLE 41

4-Demethoxy-4-isobutyloxy-N-trifluoroacetyldaunomycin 0.7 g. of 4-demethoxy-4-isobutyloxydaunomycinone was treated with 0.63 g. of 2,3,6-trideoxy-3-trifluoroacetamido-4-O-trifluoroacetyl-α-L-lyxopyranosyl chloride in the presence of 0.5 g. of silver trifluoromethansulfonate as described in Example 6, to give 0.3 g. of 4-demethoxy-4-isobutyloxy-N-trifluoroacetyldaunomycin.

EXAMPLE 42

4-Demethoxy-4-isobutyloxydaunomycin hydrochloride 0.25 g. of 4-demethoxy-4-isobutyloxy-N-trifluoroacetyldaunomycin was treated with aqueous 0.15 M NaOH solution, as described in Example 7, to give 0.080 g. of 4-demethoxy-4-isobutyloxydaunomycin hydrochloride.

BIOLOGICAL ACTIVITY

The 4-alkoxy (or aryloxy) daunomycin analogues were tested under the auspices of N.C.I. — National Institute of Health, Bethesda, Md., against Lymphocytic Leukemia $P_{388}$ according to the procedure described in Cancer Chemotherapy Reports, Part 3, Vol. 3, page 9 (1972). The following Table illustrates the anti-tumor activity of some of the anthracyclines of the invention.

The new compounds were compared to daunomycin in a test consisting of mice infected with tumor cells: the injections are made on days 5, 9, 13 with a 4 day interval between each single injection starting from the fifth day after tumor transplantation in the mice.

TABLE

| Compound | Schedule of Treatment in days (i.p.) | Dose mg./kg. | T/C % |
|---|---|---|---|
| Daunomycin . HCl | 5, 9, 13 | 32.0 | 101 |
|  |  | 16.0 | 119 |
|  |  | 8.0 | 144 |
|  |  | 4.0 | 122 |
|  |  | 2.0 | 112 |
| 4-demethoxy-4-ethoxy-Daunomycin . HCl | 5, 9, 13 | 50.0 | 119 |
|  |  | 25.0 | 131 |
|  |  | 12.5 | 119 |
|  |  | 6.25 | 110 |
|  |  | 3.13 | 91 |
| 4-demethoxy-4-isopropyloxy-Daunomycin . HCl | 5, 9, 13 | 50.0 | 89 |
|  |  | 25.0 | 135 |
|  |  | 12.5 | 162 |
|  |  | 6.25 | 118 |
|  |  | 3.13 | 126 |
| 4-demethoxy-4-benzyloxy-Daunomycin . HCl | 5, 9, 13 | 50.0 | 155 |
|  |  | 25.0 | 99 |
|  |  | 12.5 | 107 |
|  |  | 6.25 | 107 |
|  |  | 3.13 | 105 |
| 4-demethoxy-4-cyclohexyloxy-Daunomycin . HCl | 5, 9, 13 | 50.0 | 122 |
|  |  | 25.0 | 110 |
|  |  | 12.5 | 103 |
|  |  | 6.25 | 109 |
|  |  | 3.13 | 108 |

Variations and modifications can, of course, be made without departing from the spirit and scope of the invention.

Having thus described our invention, what we desire to secure by Letters Patent and hereby claim is:

1. A compound of the formula:

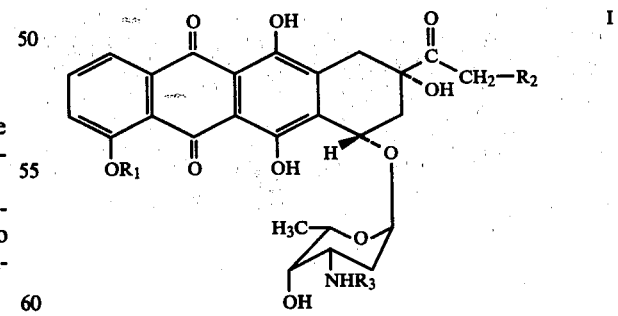

wherein $R_1$ is a $C_3$-$C_6$ cycloalkyl; a $C_3$-$C_6$ cycloalkyl substituted by a halogen, hydroxy, methoxy, amino or dimethylamino group; phenyl or phenyl substituted with nitro, chlorine or methoxy; thiazyl, pyridyl, pyrazyl; or phenyl-alkyl group of the formula X—Phe—$(CH_2)_n$—, in which X is hydrogen, halogen, hydroxyl, amino, or nitro, and n is an integer from 1 to 2;

$R_2$ is hydrogen, hydroxyl or acyloxy (R—COO—), where R is an alkyl having from 1 to 11 carbon atoms; and $R_3$ is hydrogen or trifluoroacetyl and salts thereof with pharmaceutically acceptable acids.

2. A compound according to claim 1, which is 4-demethoxy-4-benzyloxy-N-trifluoroacetyldaunomycin.

3. A compound according to claim 1, which is 4-demethoxy-4-benzyloxy-daunomycin hydrochloride.

4. A compound according to claim 1, which is 4-demethoxy-4-cyclohexyloxy-N-trifluoroacetyldaunomycin.

5. A compound according to claim 1, which is 4-demethoxy-4-cyclohexyloxydaunomycin hydrochloride.

6. A pharmaceutical composition for inhibiting the growth of lymphocytic leukemia $P_{388}$ comprising a compound according to claim 1 in an amount sufficient to inhibit the growth thereof.

7. A method of inhibiting the growth of Lymphocytic leukemia $P_{388}$ which comprises administering to a host afflicted therewith, a compound according to claim 1, in an amount sufficient to inhibit the growth thereof.

8. A method according to claim 7, wherein said compound is administered intraperitoneally.

* * * * *

UNITED STATES PATENT AND TRADEMARK OFFICE
CERTIFICATE OF CORRECTION

PATENT NO. : 4,166,848
DATED : September 4, 1979
INVENTOR(S) : LUIGI BERNARDI et al It is certified that error appears in the above—identified patent and that said Letters Patent is hereby corrected as shown below:

Column 6, line 51: "was treated with 10 ml. if isopropyliodide"

should read -- was treated with 10 ml. of isopropyliodide --.

Column 7, line 7: "triethoxycarbonyldaunomycinone ,$0^{in}$ 200"

should read -- triethoxycarbonyldaunomycinone in 200 --.

Column 8, line 24: "and evaported to dryness." should read

-- and evaporated to dryness. --.

Column 8, line 35: "triethylcarbonyldaunomycinone" should read

-- triethoxycarbonyldaunomycinone --.

Signed and Sealed this

Twenty-ninth Day of December 1981

[SEAL]

*Attest:*

GERALD J. MOSSINGHOFF

*Attesting Officer*     *Commissioner of Patents and Trademarks*